US00PP30174P3

(12) United States Plant Patent
Braun

(10) Patent No.: US PP30,174 P3
(45) Date of Patent: Feb. 5, 2019

(54) APPLE TREE NAMED 'FUJI VW'

(50) Latin Name: ***Malus domestica* Borkh.**
Varietal Denomination: Fuji VW

(71) Applicant: KIKU SRL GmbH, Girlan/Eppan (IT)

(72) Inventor: Jürgen Braun, Girlan (IT)

(73) Assignee: KIKU SRL GmbH, Girlan/Eppan (IT)

( * ) Notice: Subject to any disclaimer, the term of this patent is extended or adjusted under 35 U.S.C. 154(b) by 0 days.

(21) Appl. No.: 15/530,916

(22) Filed: Mar. 22, 2017

(65) Prior Publication Data

US 2017/0280601 P1 Sep. 28, 2017

(30) Foreign Application Priority Data

Mar. 24, 2016 (QZ) ..... PBR 2016/0823

(51) Int. Cl.
*A01H 5/08* (2018.01)

(52) U.S. Cl.
USPC ..... Plt./168

(58) Field of Classification Search
USPC ..... Plt./161, 168
See application file for complete search history.

*Primary Examiner* — Susan McCormick Ewoldt
(74) *Attorney, Agent, or Firm* — Michelle Bos Legal LLC

(57) ABSTRACT

'Fuji VW' apple is a 'Fuji' sport notable for its fruit, which is fully colored well before harvest, and has a distinctive solid red-purple overcolor. 'Fuji VW' can be harvested in a single picking.

6 Drawing Sheets

Latin name: *Malus domestica* Borkh.
Variety denomination: 'Fuji VW'.

BACKGROUND OF THE VARIETY

'Fuji VW' is a new and distinct variety of apple tree (*Malus domestica* Borkh), which originated as a limb sport mutation of 'Brak' Fuji (U.S. Plant Pat. No. 15,261). 'Fuji VW' was discovered by the inventor in a cultivated orchard at Girlan, Eppan, Italy in 2009, and was selected for further observation for its vigorous spur production and distinctive early and even coloring of fruit. 'Fuji VW' was first asexually propagated by chip budding in 2010 at Presina, Italy, and has since been observed to remain true to type over successive asexually propagated generations.

BRIEF DESCRIPTION OF THE VARIETY

'Fuji VW' was first selected for its spur vigor and for its fruit, which is fully colored well before harvest. A comparison of 'Fuji VW' to parent 'Brak' Fuji and to similar varieties 'Aztec' Fuji (not patented) and 'Fuji Fubrax' (U.S. Plant Pat. No. 18,761) is set forth below.

TABLE 1

Comparison of 'Fuji VW' to 'Brak' Fuji

| | 'Fuji VW' | 'Brak' Fuji |
|---|---|---|
| Anthocyanin coloration at base of petiole | Substantial | Minimal |
| First bloom | April 4 | April 10 |
| Fruit overcolor | Red-purple | Red |

TABLE 2

Comparison of 'Fuji VW' to 'Aztec' Fuji

| | 'Fuji VW' | 'Aztec Fuji' |
|---|---|---|
| Relative area of fruit overcolor | Large to very large | Very large—100% |
| Color of fruit stalk | Light brown | Dark brown |
| Shoot internode length | 2.5 cm | 3.0 cm |
| Color of upper leaf surface | Green | Yellow-green |
| Stem color | Brown | Orange-brown |

TABLE 3

Comparison of 'Fuji VW' to 'Fuji Fubrax'

| | 'Fuji VW' | 'Fuji Fubrax' |
|---|---|---|
| Tree vigor | Vigorous, compact | Standard |
| Tree habit | Spreading | Drooping |
| Pubescence on one-year-old shoot | Weak | Medium to strong |
| Leaf color | Dark green | Medium to dark yellow-green |
| Fruit overcolor | Red-purple | Red |
| Pattern of fruit overcolor | Solid flush | Solid flush with strongly defined stripes |
| Timing of fruit coloration | Early; homogeneous full color a month before harvest | Late |
| Fruit stalk length | Short | Medium to long |
| Depth of stalk cavity | Medium | Deep |
| Depth of eye basin | Medium | Deep |
| Harvest | 100% of fruit harvested at first pick | 50% to 80% of fruit harvested at first pick |

BRIEF DESCRIPTION OF THE PHOTOGRAPHS

Figure 1:
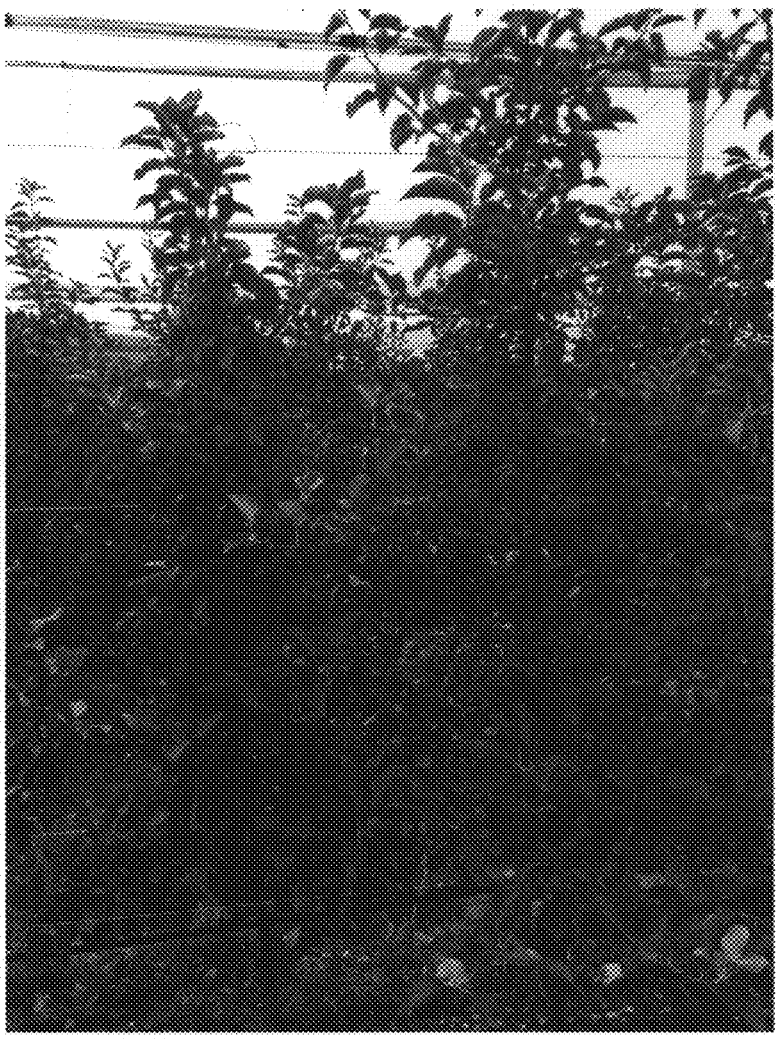
Figure 2:
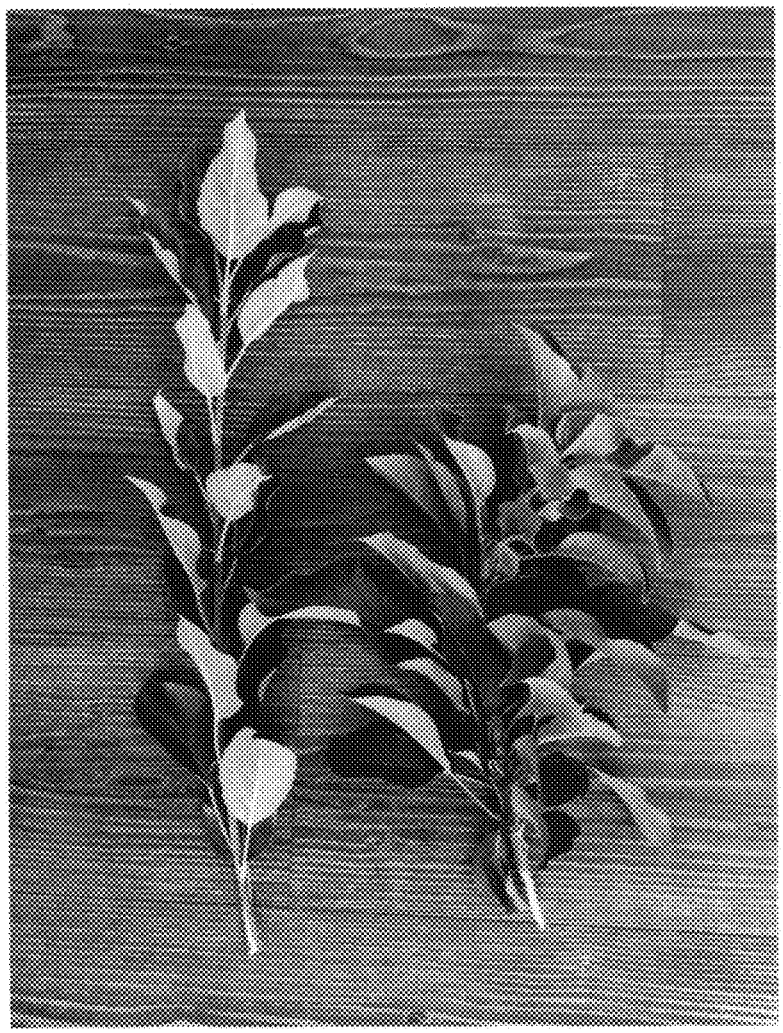
Figure 3:
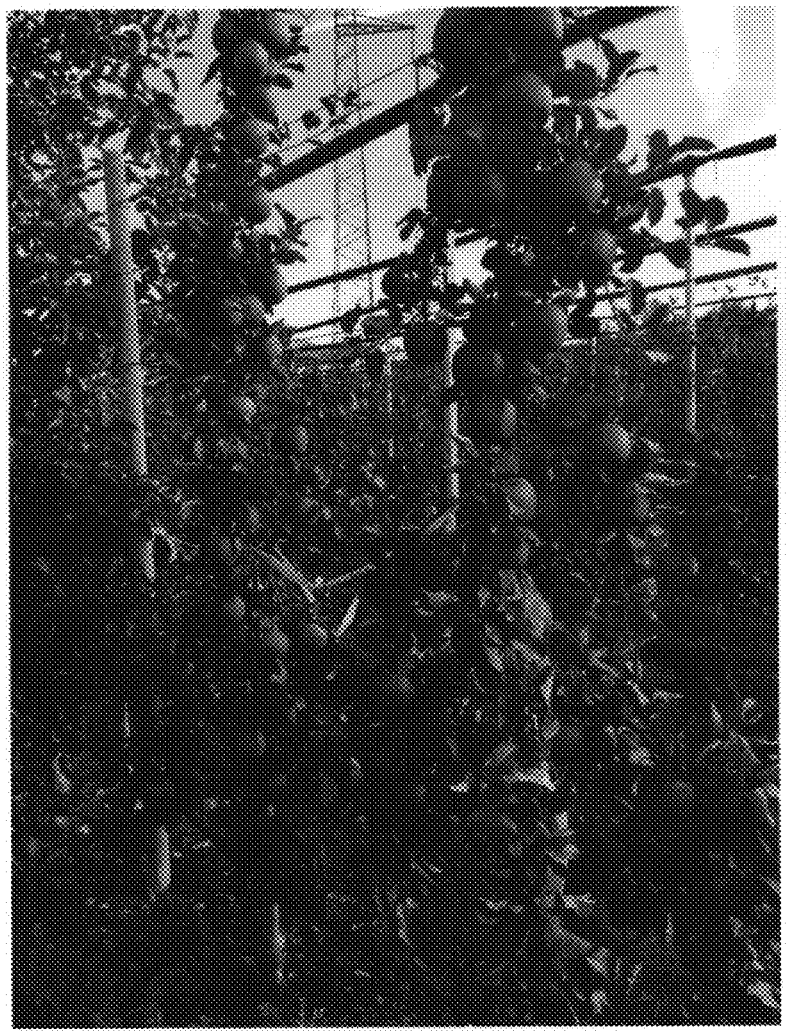
Figure 4:
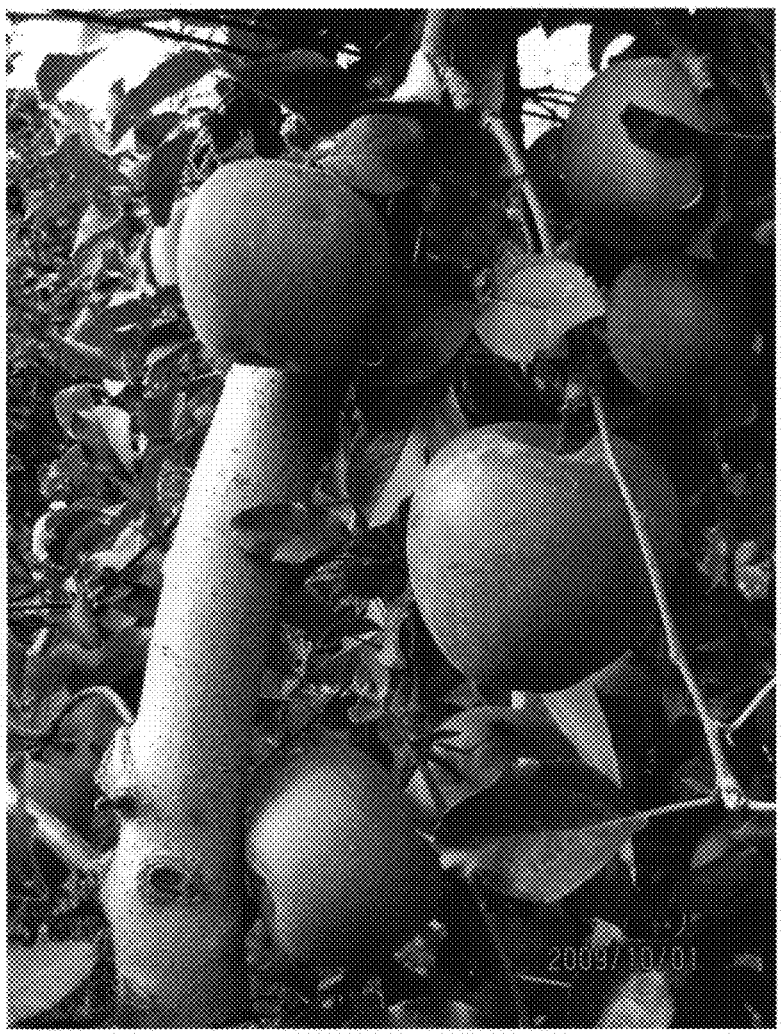
Figure 5:
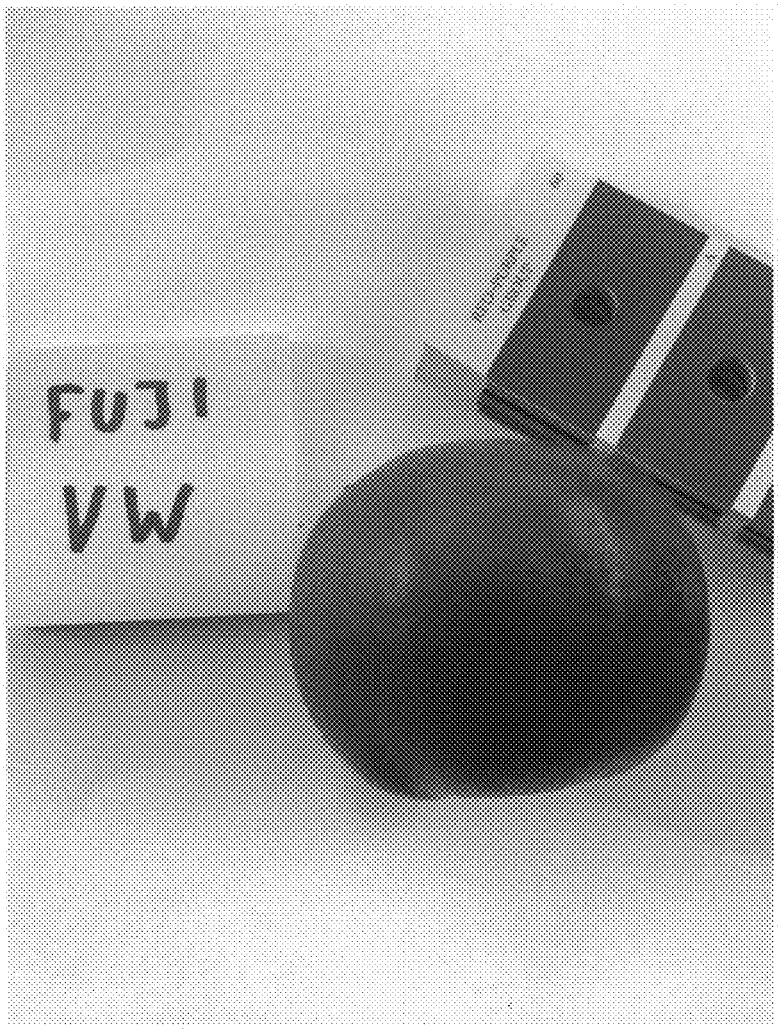
Figure 6:
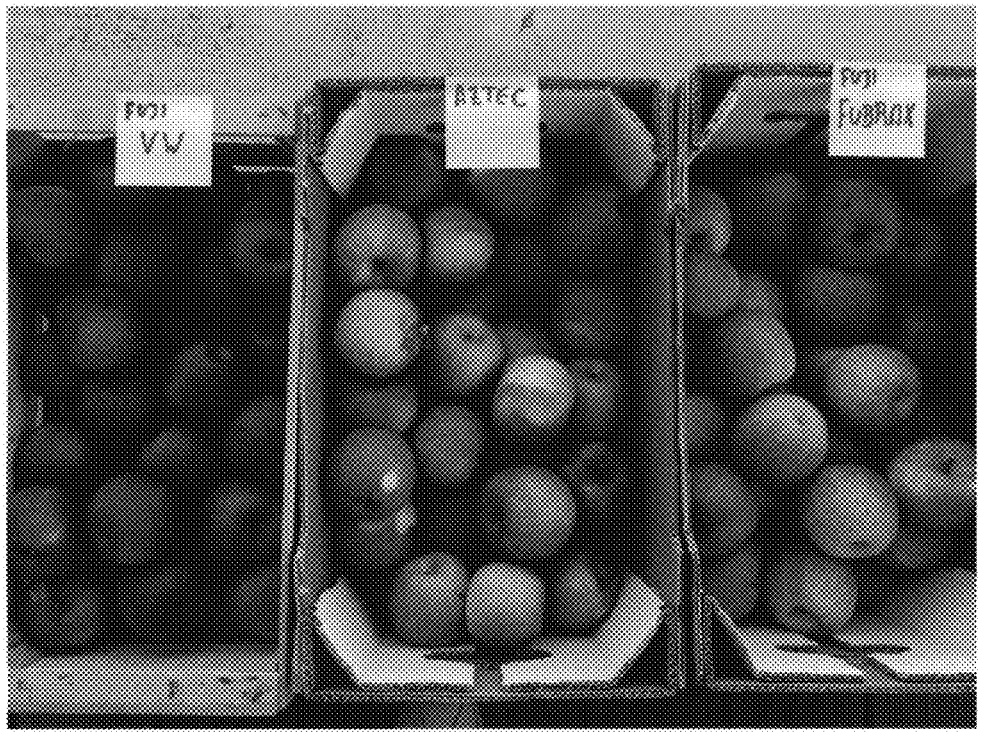

FIG. 1 shows 'Fuji VW' trees;
FIG. 2 shows branches and leaves of 'Fuji VW';

FIG. 3 shows trees and fruit of 'Fuji VW';
FIG. 4 shows the trunk and fruit of 'Fuji VW';
FIG. 5 shows a fruit of 'Fuji VW'; and,
FIG. 6 shows fruit of 'Fuji VW' with comparison varieties 'Aztec' and 'Fuji Fubrax'.

DETAILED BOTANICAL DESCRIPTION OF THE VARIETY

The following detailed botanical description of 'Fuji VW' apple tree is based on observations made during the 2014 and 2015 growing seasons at Cornaiano, Italy of trees planted in 2012 on M9 T337 virus free rootstock. All colors are described according to The Royal Horticultural Society Colour Chart (2001). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
- *Vigor.*—Vigorous production of spurs.
- *Type.*—Ramified.
- *Habit.*—Spreading, compact.
- *Trunk diameter* (*at* 30 *cm above the graft*).—2.3 cm+−0.2 cm.
- *Bark texture.*—Smooth.
- *Bark coloration.*—Greyed-green 197A.
- *Type of bearing.*—On spurs and long shoots.

Branch (fruiting branches located at around 1 m above the graft union):
- *Length.*—30 cm to 70 cm.
- *Diameter.*—1.1 cm+−0.1 cm at 5 cm to the stem.
- *Crotch angle.*—110 degrees+−10.
- *Bark color.*—Grey-brown N199A.
- *Lenticel length.*—0.19 cm+−0.07.
- *Lenticel color.*—Orange-white 159A.
- *Number of lenticels per cm*$^2$.—8+−2.

One year old shoot:
- *Length.*—50 cm+−10.
- *Color.*—Greyed-orange 166A.
- *Pubescence.*—Very weak.
- *Thickness.*—0.5 cm+−0.1.
- *Internode length.*—2.5 cm+−0.5.
- *Number of lenticels per cm*$^2$.—6+−2.

Flower buds:
- *Quantity per spur.*—6.
- *Shape.*—Oval.
- *Length.*—0.6 cm.
- *Diameter.*—0.4 cm.
- *Color.*—Greyed-green N187A.

Flowers:
- *Diameter of fully open flower.*—4.7 cm+−0.2.
- *Relative position of petal margin.*—Touching.
- *Number per cluster.*—5 plus king flower.
- *Date of first bloom.*—April 4.
- *Date of full bloom.*—April 17.
- *Pollination requirement.*—'Gala' is an acceptable pollenizer.

Petals: All measured on king flower.
- *Number per flower.*—5.
- *Shape.*—Oval.
- *Length.*—2.4 cm+−0.2.
- *Width.*—1.4 cm+−0.2.
- *Apex.*—Round.
- *Base.*—Pointy.
- *Margin.*—Unruffled.
- *Color of upper surface.*—White 155A.
- *Color of lower surface.*—White 155A.

Stigma:
- *Position.*—Above anthers, similar to 'Golden Delicious'.
- *Size.*—0.08 cm+−0.1.
- *Color.*—Yellow 5A.

Style:
- *Size.*—1.0 cm+−0.2.
- *Color.*—Yellow-green 145A.

Ovary:
- *Size.*—0.5 cm+−0.1.
- *Color.*—Yellow-green 144A.

Anthers:
- *Quantity.*—10+−2.
- *Size.*—0.6 cm+−0.1.
- *Color of anther.*—Yellow 17A.

Pedicel:
- *Length.*—3.0 cm+−0.8.
- *Diameter.*—0.16 cm+−0.02.
- *Color.*—Yellow-green 145A.

Sepals:
- *Quantity.*—5.
- *Color.*—Green 145A.
- *Shape.*—Pointy, triangular.
- *Margin.*—Smooth.
- *Length.*—0.75 cm+−0.05.

Leaves:
- *Shape.*—Elliptic.
- *Length.*—Up to 11 cm.
- *Width.*—Up to 6 cm.
- *Length/width ratio.*—2+−0.1 to 1.
- *Blade margin.*—Serrate.
- *Apex.*—Acuminate.
- *Base shape.*—Cuneate.
- *Division.*—Simple.
- *Venation.*—Reticulate.
- *Vein color.*—Yellow-green 145A.
- *Color of upper surface.*—Green 139A.
- *Color of lower surface.*—Green 138B.
- *Attitude in relation to shoot.*—Upward.

Petiole:
- *Length.*—3.9 cm+−0.1.
- *Diameter.*—1.5 cm+−0.1.
- *Color, upper surface.*—Green 138A.
- *Color, lower surface.*—Green 143C.
- *Anthocyanin at base.*—Red-purple 59C.
- *Stipule length.*—10 mm.
- *Stipule color.*—Yellow-green 147A.

Fruit:
- *Quantity per cluster.*—5 maximum.
- *Diameter.*—87 mm+−7.
- *Weight.*—285 g+−25.
- *Ratio of height to width.*—1 to 1.
- *General shape in profile.*—Globose.
- *Position of maximum diameter.*—Equator.
- *Ribbing.*—Absent or weak.
- *Crowning at calyx end.*—Absent or weak.
- *Size of eye.*—Small, 1 cm deep.
- *Aperture of eye.*—2.9 cm+−0.2.
- *Length of sepal.*—Medium, 0.45 cm.

*Bloom of skin.*—Medium.
*Greasiness of skin.*—Absent.
*Background color of skin.*—Not visible.
*Amount of over color.*—100%.
*Over color of skin.*—Red-purple 60A.
*Intensity of over color.*—High.
*Pattern of over color.*—Only solid flush.
*Amount of russet around stalk cavity.*—Absent or small.
*Amount of russet on cheeks.*—Absent.
*Area of russet around eye basin.*—Absent.
*Length of stalk.*—Short, 1.9 cm+−0.3.
*Thickness of stalk.*—Medium, 0.4 cm+−0.1.
*Depth of stalk cavity.*—Medium, 1.3 cm+−0.1.
*Width of stalk cavity.*—Broad, 2.9 cm+−0.1.
*Firmness of flesh.*—Medium, 6.5 kg per $cm^2$.
*Flesh texture.*—Crunchy.
*Aroma.*—Sweet.
*Juiciness.*—Very juicy.
*Brix.*—14 to 15° Brix.
*Flesh color.*—Yellow 10D.
*Number of lenticels per $cm^2$.*—5+−2.
*Size of lenticels.*—Large, up to 2.5 mm.
*Aperture of locules.*—Moderately open.
*Stem coloration.*—Greyed-orange 177A.

Seeds:
*Quantity per fruit.*—Max 2 per chamber, max 10 total.
*Shape.*—Teardrop.
*Length.*—0.8 cm+−0.1.
*Width.*—0.5 cm+−0.1.
*Color.*—Greyed-orange 177A.

Harvest:
*Time for harvest.*—Mid-October, similar to standard 'Fuji'.
*Number of picks.*—1.
*Amount of fruit produced per tree per harvest.*—20 kg+−2.

Disease resistance/susceptibility: Similar to other 'Fuji'-types.

Market use: Fresh market.

Storageability: Stores well from picking time up to April under proper storage conditions.

The invention claimed is:

1. I claim a new and distinct apple tree, substantially as described and illustrated herein.

* * * * *